(12) United States Patent
Belmont

(10) Patent No.: US 9,273,324 B2
(45) Date of Patent: Mar. 1, 2016

(54) RECOMBINANT GENE EXPRESSION

(76) Inventor: Andrew S. Belmont, Urbana, IL (US)

( * ) Notice: Subject to any disclaimer, the term of this patent is extended or adjusted under 35 U.S.C. 154(b) by 779 days.

(21) Appl. No.: 12/960,541

(22) Filed: Dec. 5, 2010

(65) Prior Publication Data

US 2012/0142049 A1 Jun. 7, 2012

(51) Int. Cl.
*C12P 21/00* (2006.01)
*C12P 19/34* (2006.01)
*C12N 15/85* (2006.01)

(52) U.S. Cl.
CPC ..................................... *C12N 15/85* (2013.01)

(58) Field of Classification Search
CPC ...................................................... C12N 15/85
USPC ................................................ 435/69.1, 91.1
See application file for complete search history.

(56) References Cited

PUBLICATIONS

Bian et al. (Apr. 2010) BAC TG-EMBED: one-step method for high-level, copy-number-dependent, position-independent transgene expression. Nucleic Acids Research, pp. 1-13.*
Hu et al. (Apr. 2009) Large-scale chromatin structure of inducible genes: transcription on a condensed, linear template. J. Cell Biology 185(1): 87-100.*
Blaas et al. (Jan. 2009) Bacterial artificial chromosomes improve recombinant protein production in mammalian cells. BMC Biotechnology 9: 3 (pp. 1-5).*
Okita et al. (2007) Generation of germline-competent induced pluripotent stem cells. Nature 448: 313-318.*
Clarke et al. (1997) Murine mucopolysaccharidosis type 1: targeted disruption of the murine a-L-iduronidase gene. Human Molecular Genetics 6(4): 503-511.*
Giel-Moloney et al. (2007) Ubiquitous and uniform in vivo fluorescence in ROSA26-EGFP BAC transgenic mice. Genesis 45: 83-89.*
Yang et al. (2005) An overview on the generation of BAC transgenic mice for neuroscience research. Current Protocols in Neuroscience Suppl. 31: 5.20.1-5.20.11.*
Garrick et al Nat Genet. 18:56-59, 1998, abstract only.*
Shizuya et al Proc Natl Acad Sci U S A, 1992, 89:8794-1992.*
Hu et al (J. Cell Biol, 2009, 185, 87-100.*
Kireev et al, Nat Methods., 2008 5:311-313.*
Williams et al, BMC Biotechnology 2005, 5:17, 1-9.*
Bowtell et al Journal of Virology, 1988, p. 2464-2473.*
Denoeud et al., 2007 Genome Res. 17:746-759.*

* cited by examiner

*Primary Examiner* — Anoop Singh
(74) *Attorney, Agent, or Firm* — Richard Aron Osman

(57) ABSTRACT

Genes are expressed by culturing cells comprising a host chromosome comprising an integrated artificial chromosome comprising recombinant genes, under conditions whereby each recombinant gene is expressed copy number dependently and position independently. Deletions increase expression from recombinant gene(s) inserted into the artificial chromosome.

9 Claims, 7 Drawing Sheets

RECOMBINANT GENE EXPRESSION

Figure 1:
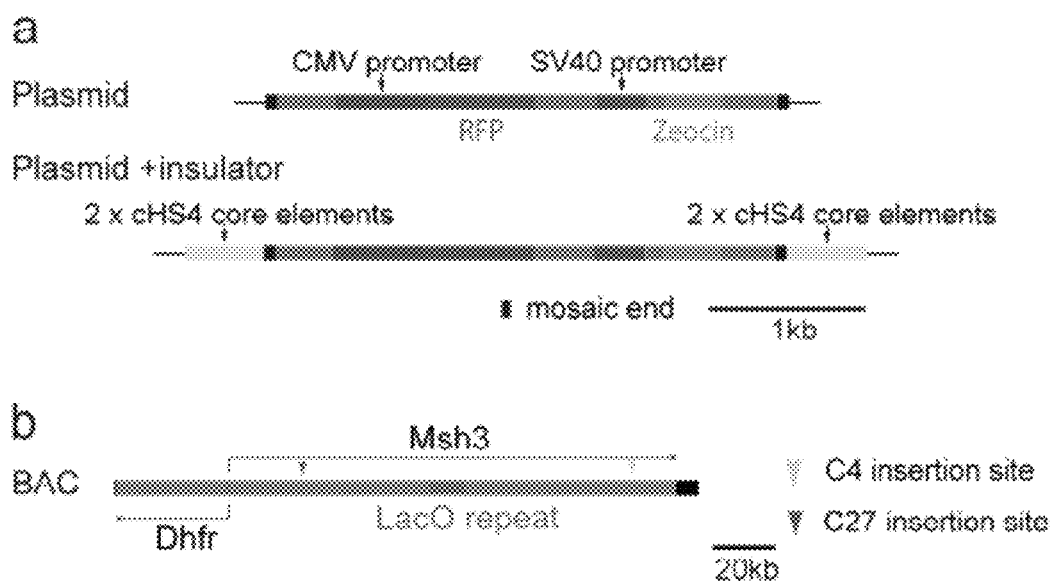

This invention was made with government support under Grant Numbers R01 GM058460 and R01 GM042516, awarded by the National Institutes of Health (NIH). The government has certain rights in the invention.

The field of the invention is improved recombinant gene expression.

INTRODUCTION

This invention provides a method for improved expression of single and multiple recombinant genes introduced back into higher eukaryotic cells and, in particular, mammalian cells. Reliable expression of genes created by recombinant DNA methods and introduced back into cells is an important technical goal over a wide range of applied and basic areas of molecular biological and biomedical research. For example, protein biopharmaceuticals currently represent a rapidly growing, tens of billions dollar market, yet engineering high level gene expression of recombinant proteins remains a major bottleneck to new biopharmaceutical development decades after the first successful mammalian gene transfection. In applications such as gene therapy, problems in engineering stable gene expression become even more severe as expression must be maintained through cell differentiation and over months or years. All of these problems are magnified multiplicatively when it comes to engineering simultaneous expression of multiple recombinant genes. This is highlighted by recent work demonstrating the induced dedifferentiation of somatic cells to create induced pluripotent stem cells (iPSCs), which resemble embryonal stem cells (ESCs), by the expression of four or more recombinant genes. Non-reproducible expression of the four transgenes has already become recognized as an important factor limiting efficiency of reprogramming as evidenced by the greatly improved efficiency of secondary versus primary reprogramming (Hockemeyer et al. 2008; Maherali et al. 2008; Wernig et al. 2008; Woltjen et al. 2009; Carey et al. 2010). Variations in reprogramming efficiency from 1-29% and clear effects of gene dosage and chromosome position effects, including variegated expression, suggest that transgene expression remains a large contributing factor to reprogramming efficiency. Moreover, secondary iPSC reprogramming efficiency reaches as high as 65% in immortalized cells and 80% using p53−/− knockout iPS cell-derived, secondary MEFs (Utikal et al. 2009). These results suggest that similarly high primary iPS cell reprogramming efficiencies might be reached if reliable reprogramming factor expression could be combined with addition of a limited number of additional factors. Expressing multiple transgenes for cell reprogramming and trans-differentiation is tremendously more problematic than expressing a single gene, as the probability of expressing simultaneously each of these transgenes at satisfactory levels is the product of the probabilities for each individual transgene. Multi-gene expression is now best implemented by expression from a single promoter, using IRES or viral 2A-like peptide sequences (Szymczak et al. 2004) to "link" the individual transgenes. This solution is limited to a few genes and does not allow independent gene regulation through the use of individual promoters.

The original method for expressing exogenous, recombinant genes in mammalian cells remains still one of the most common methods used today in a wide range of eukaryotic species. Linking several DNA sequence regulatory elements with a cDNA coding sequence for a gene creates what is called a mini-gene. These regulatory elements typically include an enhancer/promoter sequence, a poly-adenylation signal, and optionally an intron sequence, which empirically seems to improve RNA processing and export out of the nucleus. Typically, viral enhancer/promoters have been used as they are found to produce strong expression. Similarly, viral poly-adenylation and intron sequences have been used as well. Alternatively promoters from known, highly expressed genes are used, as are other regulatory elements from known, endogenous genes. Synthetic promoters comprised of combinations of different, engineered regulatory cis and trans elements from other species, and even prokaryotic species, have been used as well. It is quite common to mix regulatory sequences from different sources to produce the mini-gene. In cases in which the DNA sequence of the endogenous gene is not too long, a copy of the actual endogenous gene itself, used either with the regulatory elements for this gene or other cis-regulatory elements as described above, can be used. For the purpose of this description, we call all of the above embodiments "recombinant genes".

These recombinant gene sequences together with a selectable marker are typically inserted into a plasmid cloning vector. Together these elements are called an expression vector because they are designed to allow expression of the recombinant gene when introduced back into eukaryotic cells. Additional cis regulatory elements may be added to this expression vector to facilitate gene expression of the recombinant gene. A key feature of these expression vectors is that they typically are smaller in sequence than the original coding sequence of the gene that is to be expressed, allowing cloning in a plasmid. The use of known regulatory elements from well-characterized genes together with cDNA sequences from the gene to be expressed provides the capability of expressing genes in different species, cell types, and at different levels from the endogenous gene. Moreover, this practice enables expression of particular genes without knowledge or use of the regulatory elements for these genes.

Transfection and random integration of the recombinant gene alone or the entire plasmid expression vector into the endogenous chromosomes of a target cell allows expression of the recombinant gene. However, several problems are typically encountered. The first is called multi-copy transgene silencing. In general, gene expression is not correlated with gene copy number, and as copy number goes up, expression per copy number tends to actually decrease, such that cells carrying hundreds to thousands of copies of the recombinant gene could show even less total expression than a cell carrying just one copy of the recombinant gene.

The second problem typically encountered is called chromosome position effect, or position dependent expression. In this case different cell clones that carry the mini-gene construct integrated randomly at different chromosomal locations show very different expression levels per gene copy even when single copies of the mini-gene are inserted. Whereas some chromosomal integration locations appear permissive for gene expression, other locations are nonpermissive, with the range of expression levels possible quite large. What this means is that only a subset of cells that have the recombinant gene show high-level expression. Other cells will not only show reduced or no expression but they may even show variegated expression, whereby cells derived from the same parent cell and carrying the recombinant gene at the same chromosomal location show different expression levels. This phenomenon is called chromosome position effect variegation.

The net result of both these problems is that expression of recombinant genes is highly unpredictable and irreproducible. Expression is typically copy number independent and position dependent such that many different cell clones need to be screened to identify a particular clone with non-variegated expression at a level close to the desired expression level. In applications such as biopharmaceutical protein production where one is interested in expressing levels of the recombinant protein as high as possible, the effect of multi-copy gene silencing reduces the ability to achieve high-level expression by inserting a larger number of copies of the recombinant gene construct.

A third problem is the instability of expression of these recombinant genes over time. During weeks or months in culture mini-gene expression often decreases and may disappear entirely due to epigenetic changes. A related but even more severe problem is a decrease or elimination of recombinant gene expression after transition from a proliferative to quiescent (non-proliferative) state or after differentiation from one cell lineage or cell type to another. This likely is related to chromosome position effects—a transcriptionally permissive chromosome location is likely to change with differentiation or transition to a quiescent state to become transcriptionally non-permissive, leading to a decrease in expression of the recombinant gene. These problems of changing expression over time are particularly severe for applications such as gene therapy or tissue engineering in which cells engineered to express exogenous genes must maintain expression in vivo for long periods of time and after cell differentiation and/or a prolonged arrest in a non-proliferative state.

Several approaches have been taken to overcome these three problems. One approach is to incorporate defined DNA regulatory sequences (cis sequences) into the expression vector. These regulatory sequences typically have either been shown to increase expression levels of the recombinant gene and/or to counteract chromosome position effects. Cis regulatory elements that appear to work by maintaining accessible chromatin structure and counteracting chromosome position effects include locus control regions (LCRs) (Grosveld et al. 1987), insulators (Chung et al. 1993; Pikaart et al. 1998), ubiquitous chromatin opening elements (UCOEs) (Antoniou et al. 2003; Williams et al. 2005), Scaffold/Matrix associated regions (SAR/MARs) (Zahn-Zabal et al. 2001; Kim et al. 2004), and antirepressor elements (STAR) (Kwaks et al. 2003). All have all been shown to improve transgene expression to varying degree (Kwaks and Otte 2006). While these cis-regulatory elements provide improvements, they have not yet solved the general problem of reproducible, high level, stable transgene expression (van Gaal et al. 2006). This may be related to the context in which these regulatory elements normally act. Attempts to isolate known sequence elements such as LCRs or boundary elements to their minimal sizes and combine them in plasmid and/or viral constructs have typically been unsuccessful in reconstituting their full activity seen in their normal chromosomal context (Guy et al. 1996; Stamatoyannopoulos et al. 1997; Rubin et al. 2000; Bharadwaj et al. 2003; Truffinet et al. 2005).

One aspect of the abnormal context created by reporter constructs when stably integrated into the endogenous chromosome is a heterochromatic environment not conducive to transcription. This can be created by "poison" sequences contained in the bacterial DNA included in the reporter gene construct that inhibit gene expression (Lusky and Botchan 1981; Peterson et al. 1987). One characteristic of bacterial DNA is a high CpG content as compared to eukaryotic DNA. These CpG dinucleotides tend to accumulate DNA methylation at the cytosines that is associated with gene silencing. This problem can be reduced by removing the bacterial sequences of the expression vector before transfection or by using viral or transposon reporter constructs which lead to integration of the DNA region containing the recombinant gene or mini-gene while minimizing the amount of other DNA that is integrated into the host chromosome. However, because most viruses and transposons have strong DNA size constraints, the use of such vectors places a limit on the amount of additional cis regulatory regions that can be added to the recombinant gene construct to improve expression.

Similarly, it is likely that the phenomenon of multi-copy gene silencing is related to the formation of a heterochromatin environment similarly nonconductive to transcription through unknown mechanisms. Creation of a special, nonpermissive chromatin environment by multi-copy gene silencing may very well counteract the effect that known cis regulatory elements have in their normal chromosome context. Multi-copy gene silencing can be avoided by use of viral and transposon vectors which integrate into the host chromosome as single copies or by using DNA transfection methods that favor single copy insertions. However, this reduces the total number of recombinant genes that are inserted into the host genome, reducing the overall expression level.

Currently, the most prevalent approach for biopharmaceutical production in mammalian cells is a method known as gene amplification (Cacciatore et al. 2010). Of 12 new biopharmaceuticals approved in the US and EU in 2004, 7/12 were produced in mammalian cell lines (Walsh 2004). CHO (Chinese Hamster Ovary) cells are commonly used due to their propensity to undergo gene amplification, a technique used to increase protein production (Barron et al. 2007). In this approach a recombinant gene is linked with a resistance marker. Once stable colonies with integrated copies of both genes are obtained, cells are subjected to progressively higher concentrations of selection. A very small fraction of surviving cells are found to have increased copy numbers of the DNA region surrounding the selectable marker, including the linked recombinant gene and flanking co-amplified genomic DNA 100 s-1000 s of kb in size from the host chromosome. With multiple rounds of increasing selection, typically hundreds of copies of the DHFR minigene and linked recombinant gene can be obtained. However, the amplified chromosome regions are genetically unstable, prone to epigenetic gene silencing, and frequently undergo clone failure, such that high producing clones do not sustain their transgene protein expression level over time or after adaptation to suspension culture conditions. Despite a 6-12 month development cycle, gene amplification is still the current method of choice because it yields higher expression than one step transformation methods (Cacciatore et al. 2010), in which multicopy transgene silencing and chromosome position effects limit expression.

This gene amplification approach cannot be used for most applications involving expression of recombinant genes as it requires use of transformed cell lines in which the cells have accumulated certain mutations, as normal cells do not undergo the gene amplification process. However, this method shows that multiple copies of recombinant genes are not susceptible to multi-copy gene silencing when large regions of endogenous genomic sequence separate these copies. Moreover, because total gene expression levels do not correlate strictly with the copy number of the recombinant gene this means that the recombinant gene expression level likely depends on the nature of the flanking genomic DNA which is co-amplified.

The most direct and conceptually simple way of overcoming these problems of chromosome position effect and chromosome context has been to recombine the coding region of a recombinant gene directly into the coding region of an endogenous gene using homologous recombination. In this way, the recombinant gene is placed under the normal regulatory control of the endogenous gene, eliminating chromosome position effects. The power of this approach is that unknown regulatory regions, which may be scattered across millions of by of surrounding DNA sequence, are still included. Such recombined genes are typically expressed similarly to the normal expression pattern of the endogenous gene they replace. However, in organisms such as mammals with large genome size this recombination procedure is quite inefficient making it very time consuming and difficult to identify the cell clone carrying the correctly recombined gene. This means that for most applications this procedure is impractical, as it dramatically increases the development time and can only be used in cell types in which homologous recombination frequencies are sufficiently high. Another potential problem is that the recombinant gene will be expressed under the control of the endogenous promoter, and therefore will have the tissue expression patterns and level characteristic of the endogenous gene. For expression of multiple recombinant genes, this approach prevents independent control of expression of the different recombinant genes. For high-level expression of one or multiple genes, this approach does not allow increased expression from multiple copies of recombinant genes.

As an alternative to homologous recombination insertion of recombinant genes directly into the endogenous chromosome of the target cell, an alternative approach using bacterial artificial chromosomes (BACs) or yeast artificial chromosomes (YACs) exploits the high efficiency of homologous recombination in bacteria and yeast cells. In this alternative approach a large genomic region from the higher eukaryotic genome, typically 100 s of kb in size, is cloned within the BAC or YAC. The recombinant gene is then inserted by homologous recombination in bacteria (BACs) or yeast (YACs) into the target gene contained within this cloned DNA. Then the entire cloned region containing the recombinant gene is transfected into cells of the target organism. More specifically, a BAC or YAC containing a cloned mammalian DNA region would be used to insert a recombinant gene for expression in closely related mammalian cells. The transcribed region of the recombinant gene again would (Okita et al. 2007) be recombined into the transcribed region of a gene contained within the mammalian DNA region cloned into the BAC or YAC, such that it would fall under the regulatory control of the mammalian gene contained on the BAC or YAC. After this recombination event, the BAC or YAC is then transfected into target mammalian cells and stable clones with integrated copies of the BAC or YAC can be isolated, using a selectable marker also inserted in the BAC or YAC.

Previous work has shown that a number of mammalian genes cloned within BACs or YACs are expressed within several fold of the levels of endogenous genes (Antoch et al. 1997; Yang et al. 1997; Heintz 2000). Conventional plasmid or viral based methods typically incorporate only a few, known regulatory regions, which must be reduced in size to fit on the plasmid or viral vector. The advantage of the BAC or YAC is that there is a much larger size that can be accommodated within these artificial chromosome vectors. Therefore many regulatory regions can be included which lie within several hundred kb of the promoter regulating the cloned gene, without having to identify these possible regulatory regions or narrow their size down to that which can be cloned within the plasmid or viral vector.

Insertion of the coding region of a recombinant gene into the transcribed region of the mammalian gene cloned within a BAC has been shown to be an effective way of expressing the recombinant gene after transfection of the BAC. This method has been used for instance to express a GFP and puromycin resistance cassette in transgenic mice after homologous recombination into the coding region of the Nanog gene contained within a BAC (Okita et al. 2007). Similarly, a GFP recombinant gene has been expressed from the Rosa26 locus after insertion of its sequence into the transcribed region of the Rosa26 locus contained within a BAC and introduction of the engineered BAC into the mouse genome in transgenic mice (Giel-Moloney et al. 2007).

By insertion of multiple copies of the BAC, and/or removal of repressive elements present at the endogenous locus but not on the BAC, increased expression can be obtained beyond the single copy level that would be attained if the recombinant gene were inserted directly into the same mammalian gene on the endogenous mammalian chromosome. This has been illustrated recently by comparison of the expression from a GFP reporter gene inserted into the endogenous Rosa26 locus (Mao et al. 2001) versus expression in transgenic mice carrying multiple copies of a BAC containing the same GFP reporter gene inserted into the Rosa26 locus cloned within this BAC (Okita et al. 2007).

A limitation for both homologous recombination approaches described above is still that the expression of the recombinant gene is under control of the endogenous gene promoter. This is a problem for many applications where it would be desirable for the recombinant gene to be expressed at different levels, in different tissue types, or in response to different signals than what would be obtained placing the recombinant gene under control of the regulatory mechanisms, including the promoter, of the endogenous gene.

To overcome this limitation, a variation of the BAC homologous recombination approach described above has been developed wherein the recombinant gene is inserted into the transcribed region near (within several kb) of the promoter of the gene cloned within the BAC. However, rather than just inserting the coding region of the recombinant gene such that its expression is under the control of the gene cloned in the BAC, an entire expression cassette is inserted, with it's own regulatory sequences, including promoter, poly-adenylation signal, and possibly intron sequence. The rationale here is that the same transcriptionally permissive environment created by the regulatory sequences of the gene cloned on the BAC, will act on the promoter of the recombinant gene.

Using this approach, the human IgG1-Fc recombinant gene under the control of the synthetic CAGGS promoter was placed in the second exon of the Rosa26 gene, ~6 kb from the Rosa26 promoter contained within an ~200 kb mouse genomic region cloned within a BAC (Blaas et al. 2009). The IgG1-Fc recombinant gene was linked via an internal ribosome entry site (IRES) to the coding region for yellow fluorescent protein (YFP) so that cells expressing IgG1-Fc would also be expressing YFP as both were inserted into the BAC. Also inserted adjacent to the IgG1-Fc-IRES-YFP construct was a neo selectable marker driven by a mammalian promoter. It is unclear whether the investigators obtained copy number dependent expression for independently derived stable cell clones carrying 1-55 BAC copies. One ambiguity concerning copy number dependent expression claim is that the expression level per gene copy did not extrapolate to zero for zero BAC copies. A second ambiguity was that the mammalian cell clones used to test the copy number dependence of expression of the IgG1-Fc recombinant gene were obtained by first sorting stably selected cell clones based on their YFP expression, which should be proportional to the expression of the IgG1-Fc recombinant gene since they are both translated from the same mRNA. If all stable clones carrying this modified BAC had expressed IgG1-Fc in a copy number dependent manner, then this YFP sorting should have been unnecessary.

Patent application WO/2010/060844 ARTIFICIAL CHROMOSOME VECTOR is based on this procedure of inserting a recombinant gene or mini-gene into the BAC containing a genomic locus which maintains an "open" chromatin environment permissive to transcription of a recombinant gene inserted within this BAC (Blaas et al. 2009). Essentially, what this approach does is to overcome chromosome position effects encountered in previous recombinant gene expression approaches using vectors of small size, by inserting the recombinant gene within a large genome region, ideally from the same organism or closely related organism to the host organism, which is then inserted into the host chromosome. The same large region of genomic DNA, cloned within the BAC vector, always surrounds the recombinant gene Independent of the chromosome integration site, minimizing the effect of chromosome integration site.

The gene regulation field has traditionally focused on identification of particular regulatory DNA elements, called "cis" elements, which are thought to recruit specific proteins, called "trans" factors or transcription factors, to bring about regulation of gene expression. Current thinking in the field imagines these cis and trans factors coming together to interact in some way as to initiate transcription. Moreover, in this context an "open" chromatin environment generally means a region of nucleosomes spaced and positioned such as to allow binding of transcription factors to particular regulatory regions (Boyle et al. 2007; Boyle and Furey 2009). These regions are sometimes marked by DNaseI hypersensitivity sites, short several hundred by regions sometimes devoid of nucleosomes, or with lower nucleosome occupancy, or by several kbp regions with altered nucleosome spacing and positioning.

Implicit in the choice of inserting the recombinant gene near the promoter of the gene which is contained within the genomic region cloned within the BAC is the assumption that this "open" chromatin environment is likely to be created in a local neighborhood surrounding this promoter. Moreover, there is also the underlying assumption that specific interactions of other cis elements, and trans factors associated with these cis elements, with the promoter for a recombinant gene may depend on the location of this promoter in the local neighborhood near the location of the promoter of the gene which is contained within the genomic region cloned within the BAC.

Described above is a progression of distinct innovations for improved expression of recombinant genes. First was the use of homologous recombination to insert the coding region of the recombinant gene into the transcribed region of an endogenous gene on a chromosome of the host organism. Second, was the use of homologous recombination to perform the same manipulation on a large segment of genomic DNA cloned within an artificial chromosome, followed by transfection of this artificial chromosome into eukaryotic cells and selection of stable cell clones carrying this BAC recombinant gene. This placed the recombinant gene contained within the BAC under the control of most of the same regulatory elements of the target gene now contained within the artificial chromosome while also creating a more reproducible chromatin environment independent of the insertion site of the artificial chromosome within the host chromosome. The advantages of this second approach were that the homologous recombination was carried out in E. Coli or yeast cells, where the efficiency of homologous recombination is high, and that multiple copies of the BAC insertion could produce higher amounts of recombinant protein. Third was the idea of inserting the recombinant gene with its own promoter and regulatory regions in the neighborhood of the promoter of a gene contained within the cloned genomic region, rather than placing it under the control of this promoter. This provided the same advantages as with the original artificial chromosome approach, but also allowed control by an independent promoter that could be chosen by the scientist making the construct.

SUMMARY OF THE INVENTION

The invention provides a robust, general method for transgene expression in mammalian cells that provides high level, copy number dependent, position independent expression of multiple, different transgenes within a single vector construct. As used herein the term "transgene" is not limited to a genetic material transferred from a different species, but encompasses any DNA inserted into a chromosome, plasmid or genome by transfection.

The invention also provides an improvement over a prior single gene expression system (Blass (2009) and WO/2010/060844) by making a deletion of a promoter of the gene contained within the BAC in cases in which a recombinant gene is placed inside the BAC gene; this improvement typically yields at least a 10 fold improvement in expression.

In one embodiment the invention provides a method for expressing multiple recombinant genes, comprising culturing a cell comprising a host chromosome into which an artificial chromosome is integrated, wherein the artificial chromosome comprises multiple, different recombinant genes, under conditions whereby each recombinant gene is expressed copy number dependently and position independently.

This and subsequent embodiments encompass each and every combination of the following more particular embodiments:
  wherein each of the recombinant genes is at a different location within the artificial chromosome;
  wherein the different multiple genes are expressed from the same or different promoters.
  wherein the different, multiple recombinant genes maintain a predictable, reproducible relative expression with respect to each other, rationally designed by the choice of promoters used to drive each recombinant gene;
  wherein the multiple recombinant genes is 2, 3, 4, 5, 6 or more genes (with one transcription unit driven by a single promoter we can express multiple proteins, e.g. using IRES or 2A-like peptides, see para 003), and combining multiple such transcription units allows expression of still larger numbers of proteins;
  wherein the method comprises the antecedent step of inserting the recombinant genes into the artificial chromosome by homologous recombination;
  wherein the method comprises the antecedent step of inserting the recombinant genes into the artificial chromosome using a transposon and thereby achieving random but high efficiency insertion;
  wherein the cell is in a nonhuman transgenic animal;
  wherein the artificial chromosome, such as a BAC, is chosen containing a genomic region that would be in an open conformation only in a particular differentiated state (see, e.g. para 0127); and
  wherein the cell is ex vivo.

In another embodiment the invention provides a method of producing a plurality of different proteins in a eukaryotic cell with copy number dependent, position independent expression, comprising the steps of: a) providing a backbone of an artificial chromosome; b) recombining a corresponding plurality of nucleic acids encoding the proteins into said backbone to generate an expression vector; c) introducing said expression vector into a eukaryotic host cell to obtain a eukaryotic expression cell; d) cultivating said expression cell to produce said proteins, and optionally; e) isolating one or more or all of said proteins from the cell or medium of the cell.

This, foregoing, and subsequent embodiments encompass each and every combination of the following more particular embodiments:

- wherein said recombining is performed by homologous recombination or integrase mediated cassette exchange;
- wherein 2 to 500 copies of said vector are introduced into said host cell;
- wherein one or more or all of the proteins are secretion proteins comprising a signal peptide;
- wherein one or more or all of said proteins are selected from the group consisting of serum proteins, including immunoglobulins or fragments thereof, albumin, blood factors, polypeptide hormones, cytokines, chemokines, enzymes and growth factors.
- wherein the artificial chromosome is derived from bacteria, bacteriophage, yeast or mammals;
- wherein the artificial chromosome is selected from the group consisting of a BAC, PAC, YAC and a cosmid;
- wherein the vector comprises a regulatory element for open chromatin formation;
- wherein the vector comprises a native or heterologous promoter;
- wherein the vector comprises a locus of an abundant protein;
- wherein the vector comprises a locus of mammalian or insect origin; and
- wherein the artificial chromosome, such as a BAC with non-bacterial genomic sequence chosen to maintain an open chromatin environment (e.g. para 0127), i.e. the backbone also includes these genomic regions.

In another embodiment the invention provides a method for expressing a recombinant gene, comprising culturing a cell comprising a host chromosome into which an artificial chromosome is integrated, wherein the artificial chromosome comprises the recombinant gene, under conditions whereby the recombinant gene is expressed copy number dependently and position independently and wherein the artificial chromosome comprises a deletion that significantly increases expression from recombinant genes inserted into the artificial chromosome, as compared to without the deletion.

This, foregoing, and subsequent embodiments encompass each and every combination of the following more particular embodiments:

- wherein the deletion minimizes the DNA sequences for a given genomic region cloned within the artificial chromosome that are needed to create the permissive environment for expression of the recombinant gene;
- wherein the deletion deletes the promoter of the recombinant gene;
- wherein the deletion provide at least a 10-fold fold improved expression per copy of the recombinant gene/artificial chromosome;
- wherein the deletion deletes the promoter of the recombinant gene, wherein prior to deletion, the promoter was a large genomic distance away from the location of the recombinant gene.

The foregoing embodiments may further comprise the subsequent step of isolating and/or purifying the protein(s).

The invention also provides expression vectors adapted for use in the subject methods, comprising an artificial chromosome comprising corresponding genes encoding the proteins, wherein expression in a suitable host eukaryotic cell provides copy number dependent, position independent expression.

The invention also provides transgenic cells, not in a human and comprising the subject vectors.

The invention provides the subject artificial chromosome constructs containing foreign nucleic acid sequences and methods of using these constructs for ex vivo production of proteins, like secretion proteins.

The artificial chromosomes contain replication origin sequences needed for replication and preservation over cell divisions in the respective cell used for DNA amplification, and optionally selection markers, usually antibiotic resistance. Preferred embodiments use BAC (e.g. Rosa26BAC), YAC, PAC or cosmids (microbial artificial chromosomes)—typically small chromosomes up to 5000 kbp, preferably 100-500 kbp. Other loci considered as open chromatin, such as bactin, Gapdh, Hprt, ribosomal proteins may be used.

The invention provides improved expression of proteins in general, and in particular industrial production of recombinant proteins, e.g. using at least 1, 5 or 100 liter fermentation broth volume, using batch or continuous fermentation.

Preferred host cells are mammalian or insect cells and cell lines, such as human, primate, mouse, hamster; examples include HEK cells, such as HEK293, CHO, COS, NSO cells, mouse lymphoblast cells, PerC6, or Sf9 cells.

The nucleic acid encoding the recombinant proteins is preferably recombined with the artificial chromosome backbone gene by recombination techniques, such as homologous recombination or cassette exchange, such as mediated by integrase, like ϕC31 integrase mediated cassette exchange.

The vector is preferably stably integrated into the chromosome of the host cell, preferably a mammalian or insect chromosome, more preferably a chromosome of human, murine or hamster origin, to provide a transgenic host.

The transgenic host cells exclude transgenic humans and typically harbor the vector within the genetic map of its chromosome, usually in conjunction with or directly linked in a locus of an abundantly expressed gene or protein, such as ribosomal proteins, cytoskeleton proteins and proteins for DNA synthesis, like DNA polymerase.

The selected locus preferably contains regulatory elements for open chromatin formation or protein expression in general. An anti-condensation enhancer may be employed, either through an element that is contained in the locus as a native enhancer, or through an exogenous, heterologous or synthetic regulatory element that provides for the expression chromatin structure.

Preferred loci are derived from the sequences of the production cell line, e.g. loci of the same type or species as the host cell, which provides for an allogenic locus. Exemplary loci include Rosa 26 or loci of abundantly expressed and essential genes, like beta-actin and other proteins of the cytoskeleton as well as ribosomal proteins.

Regulatory elements include a promoter, either a native promoter, which is contained in the native locus, or as a heterologous element, such as eukaryotic and/or prokaryotic promoters, or even dual promoters may be used. Exemplary promoters are generic ones, preferably CMV, Caggs, Tk (timidine kinase), ubiquitin C or EF2, which are commonly used for transfection. Besides the artificial promoters also natural promoters like beta-actin or ribosomal proteins can be used.

Multiple copies (at least 2, 3, 5, 10, or 50 up to 100 or 500) of the artificial chromosome are introduced into the host cell to improve the yield, particularly when more than one locus is employed to express the protein. Production yields are preferably at least 1, 3, 5, 10, 30 or 50 up to 100 or 500 pg/cell/day.

In one embodiment, the vector provides a complete expression unit containing all regulatory elements to provide for stable protein expression, and may be introduced into the host cell independent of the chromosomal integration.

BRIEF DESCRIPTIONS OF THE FIGURES

FIG. 1: (a) mRFP expression cassettes and (b) DHFR BAC map.

Figure 2:
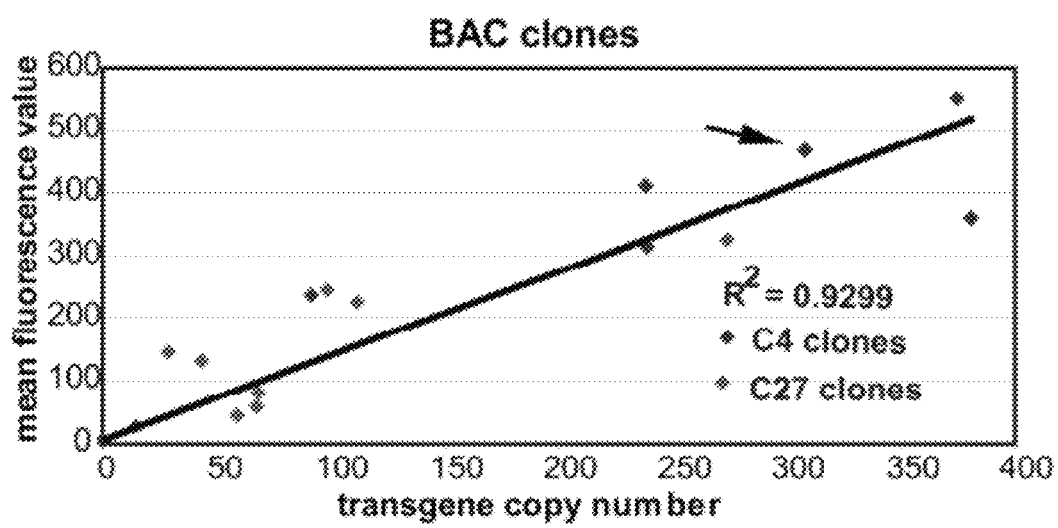

FIG. 2. Copy number dependent, position independent expression of mRFP reporter gene embedded within DHFR BAC.

Figure 3:
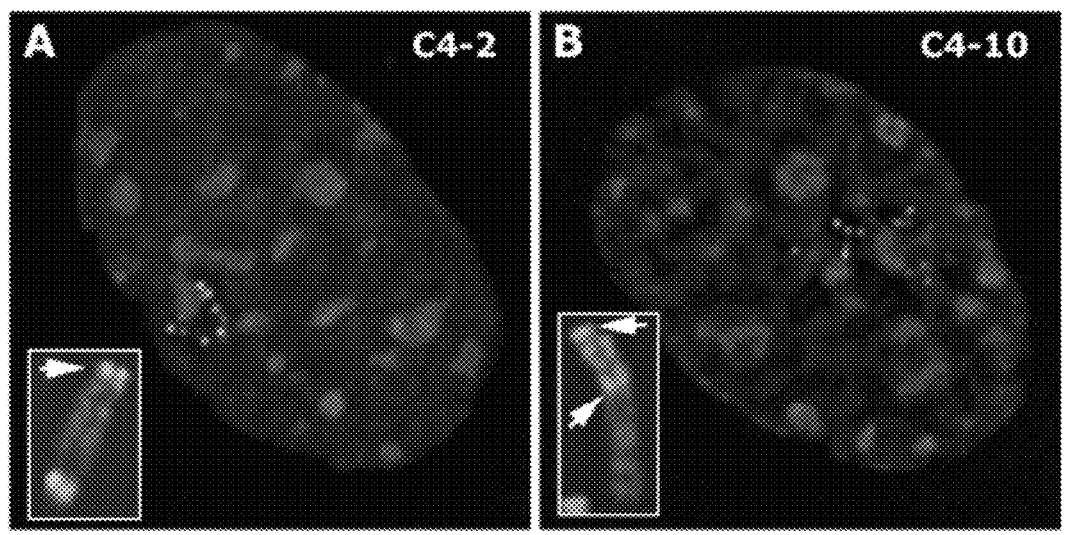

FIG. 3. DHFR BAC transgene arrays integrated towards distal end of chromosome (A) or within centromeric heterochromatin (B).

Figure 4:
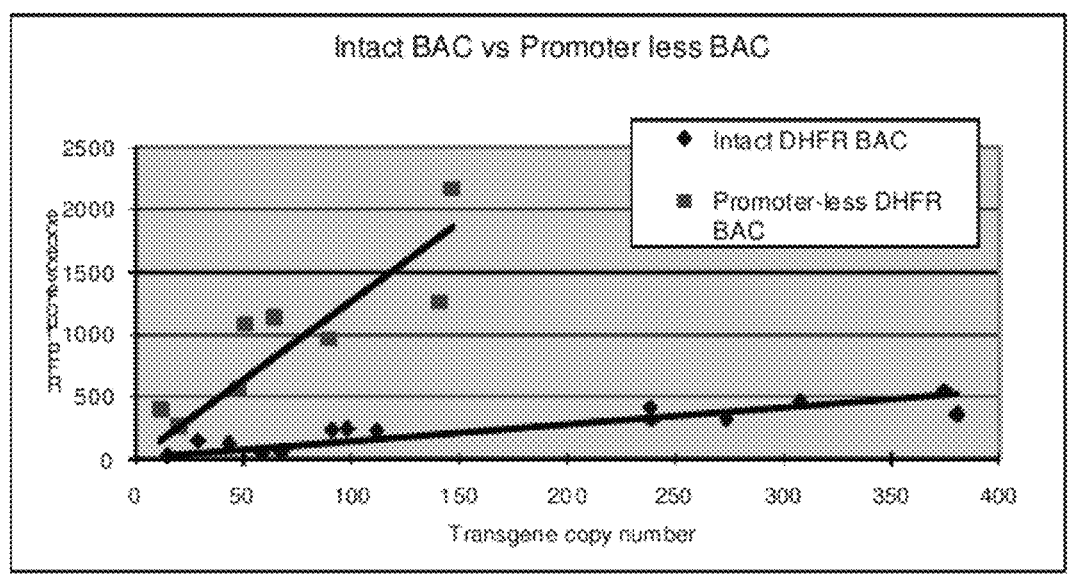

FIG. 4: Expression level versus DHFR BAC copy number for mRFP reporter placed in Msh3 intron with or without deletion of the DHFR/Msh3 divergent promoter.

Figure 5:
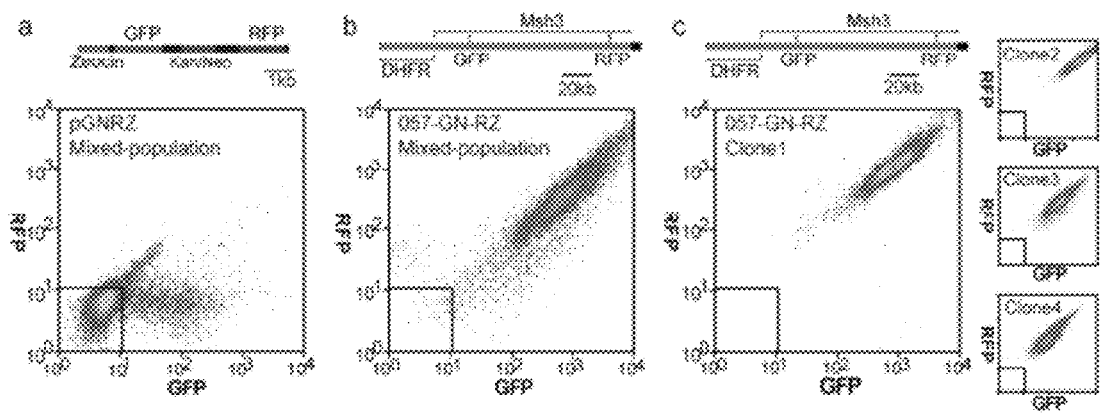

FIG. 5: Two color reporter gene assay.

Figure 6:
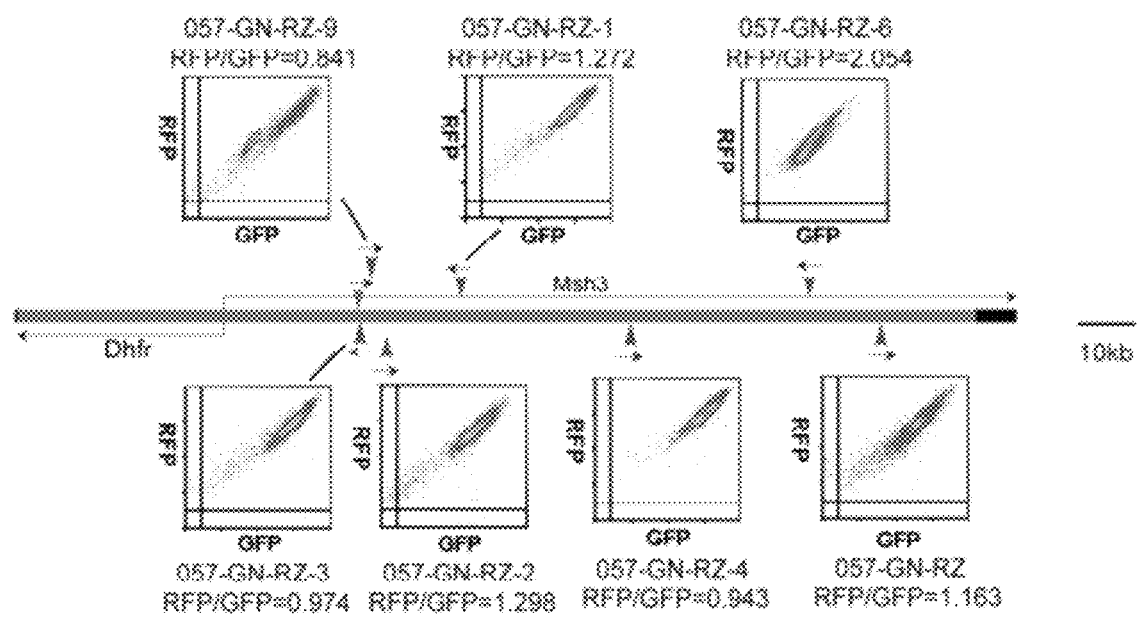

FIG. 6: Ratio of mRFP to GFP mini-gene expression near constant for a number of different positions within the DHFR BAC for the mRFP mini-gene.

Figure 7:
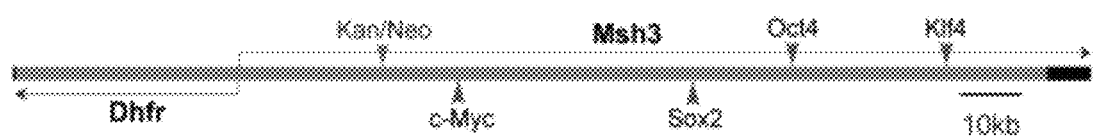

FIG. 7: Schematic showing locations of reprogramming factor genes driven by retroviral promoters, plus a selectable marker, inserted into DHFR BAC.

DETAILED DESCRIPTIONS OF THE FIGURES

FIG. 1: (a) mRFP expression cassettes showing the 19 bp Tn5 mosaic ends (black), mRFP and zeocin mini-genes, and the cHS4 insulator sequences. (b) DHFR BAC map showing BAC vector backbone (black), mouse genomic sequence (gray), 256-mer lac operator transposon (green), and mRFP expression cassette transposon insertion sites (arrowheads) for C4 (orange) and C27 (red) clones. Mouse NIH 3T3 cells were transfected with either the expression cassettes themselves (with or without the chicken HS4 insulator (a) or the DHFR BAC containing the mRFP expression cassette without insulator.

FIG. 2. Copy number dependent, position independent expression of mRFP reporter gene embedded within DHFR BAC. Spots show mean cellular fluorescence, measured by flow cytometry, versus BAC copy number, measured by qPCR, for different NIH 3T3 stable clones. Arrow points to C4-10 clone with BAC transgene array inserted into centromeric heterochromatin (FIG. 3B). Blue versus red spots correspond to clones with mRFP reporter gene inserted at two different locations within BAC.

FIG. 3. BAC array large-scale chromatin structure is independent of chromosome integration site. DHFR BAC transgene arrays integrated towards distal end of chromosome (A) or within centromeric heterochromatin (B) show similar spacing between spots of GFP-LacI binding (green) to lac operator repeats within BAC sequence. DAPI staining is blue. Insets show DNA FISH on mitotic chromosomes using a lac operator probe (red) to visualize the BAC insertions with DNA (DAPI) counterstaining (green). Arrows point to bright DAPI staining of pericentric heterochromatin, as confirmed by DNA FISH using pan-centromeric DNA FISH probe (Bian and Belmont, 2010).

FIG. 4: Expression level versus DHFR BAC copy number for mRFP reporter placed in Msh3 intron with (red) or without (blue) deletion of the DHFR/Msh3 divergent promoter. Expression per reporter gene copy increases 12× after deletion.

FIG. 5: Two color reporter gene assay: flow cytometry scatterplots show linear relationship between cellular mRFP versus EGFP reporter gene expression in mixed clonal, stable NIH 3T3 cell populations established from reporter genes embedded within the DHFR BAC (b) but not from plasmid DNA fragments with the same reporter genes (a). Boxed regions (lower left) correspond to regions of control, background fluorescence. Individual cell clones carrying BAC transgenes at a particular chromosome site show more restricted ranges of mRFP and EGFP expression but with similar ratios of mRFP and EGFP expression (c).

FIG. 6: Ratio of mRFP to GFP mini-gene expression near constant for a number of different positions within the DHFR BAC for the mRFP mini-gene. Green arrowhead points to location of GFP mini-gene which was kept fixed. Red arrowheads show different BACs with mRFP mini-gene located at those sites. Mouse NIH 3T3 cells were transfected and stable cells selected. Flow cytometry scatterplots show GFP versus mRFP fluorescence for pooled stable colonies from these transfections. Each spot in scatterplots represents measurements from one cell. The average ratio of mRFP/GFP fluorescence, shown for each BAC construct, varies from 0.84 to 2.05.

FIG. 7: Schematic showing locations of reprogramming factor genes driven by retroviral promoters, plus a selectable marker, inserted into DHFR BAC.

PREFERRED EMBODIMENTS OF THE INVENTION

The present invention provides several innovations to transgene expression technology. One is based on the idea that a distinct structural domain is created by artificial chromosome insertions into the host chromosome that may encompass the entire genomic region cloned within the artificial chromosome. Here the artificial chromosome is one of several described cloning vehicles that can carry large pieces of genomic DNA. This includes BACs, YACs, PACs, and cosmids, among others. In this case the transcriptional permissive environment created by the cloned genomic region contained within the artificial chromosome may extend over large regions or the entire region of the artificial chromosome, permitting the expression of not just one recombinant gene but multiple recombinant genes placed throughout the artificial chromosome. These recombinant genes do not have to be inserted nearby the promoters of genes contained within the genomic DNA cloned into the artificial chromosome, but can be placed throughout large regions of the cloned DNA and in some cases this may be the entire segment of genomic DNA cloned within the artificial chromosome.

Accordingly, this invention provides a method for expression of multiple recombinant genes, whereby each recombinant gene is expressed in a copy number dependent, position independent fashion when the artificial chromosome containing the recombinant genes is integrated into the host chromosome. Because a distinct structural domain is created which can facilitate transcription for a recombinant gene placed anywhere within this domain, multiple recombinant genes can be expressed reproducibly by placement at different locations within the artificial chromosome. Because similar expression can be obtained from placement of the recombinant gene throughout large regions of the artificial chromosome, simpler methods than homologous recombination can be used for insertion of the recombinant gene into the artificial chromosome, including for example use of a transposon for random but high efficiency insertion. These recombinant genes can be expressed from the same or different promoters. Importantly, not only is each of these recombinant genes expressed in a copy number dependent, position independent fashion but they maintain a predictable, reproducible relative expression with respect to each other that can be rationally designed by the choice of promoters used to drive each recombinant gene.

This is a significant advantage as compared to current techniques where expression of even single recombinant genes at reproducible levels is problematic, making it very difficult to impractical to obtain higher eukaryotic cells expressing multiple recombinant genes at specific ratios to each other. For example with plasmid or viral approaches, each single expression construct would be expressed at variable levels due to problems with multi-copy transgene silencing and chromosome position effects as described above. Simultaneous transfection with multiple expression vectors, each expressing a different recombinant gene, would lead to widely different ratios of expression of the different recombinant genes. If, for example, each recombinant gene was expressed at suitable levels in only 20% of the stable cell clones carrying this recombinant gene, then the probability of a given stable cell clone expressing satisfactory levels of two or three different recombinant genes would be 4% or 0.8%, respectively. Alternatively, each different recombinant gene cloned into a separate expression vector could be transfected sequentially. Specifically, a first recombinant gene could be transfected and stable cell clones obtained. After selecting cell clones with suitable expression levels, these cells could then be transfected with a second expression vector expressing a different recombinant gene, and stable cell clones selected which express suitable levels of the second recombinant gene. This could be repeated additional times for more recombinant genes.

This sequential approach has two significant disadvantages. First is the time required. Each transfection and selection for stable transformants would, for example with mammalian cells, take typically 2-3 weeks, with another 2-3 weeks for selection of cells expressing the appropriate level of the transgene. Repeating this multiple times would add greatly to the required time to obtain a satisfactory cell clone expressing multiple recombinant genes. Moreover, this sequential approach may be unsatisfactory for applications where expression of multiple genes is required immediately. An example would be generation of iPS cells (induced pluripotent cells) by expression of four or more recombinant genes in somatic cells. These normal somatic cells typically are limited in the number of cell divisions they can undergo before reaching cell senescence and cell cycle arrest such that even one transfection and selection of stable transformants would not be possible. Only by simultaneous expression of multiple recombinant genes would it be possible to reprogram the somatic cells to an embryonic stem cell-like state which would then confer the ability for unlimited cell divisions and the ability to select for stable transformants.

The second disadvantage is that with the sequential approach, a different selectable marker would be required for each transfection step. Therefore expression of multiple recombinant genes would require multiple selectable markers and use of multiple drugs targeting these selectable markers. Use of multiple drugs would greatly add to the cost of the selection process. More importantly, the total number of suitable selectable markers is limited, which would therefore limit the number of recombinant genes that could be transfected.

The problem of expressing multiple recombinant genes has been sufficiently severe, that alternative approaches that involve expressing multiple recombinant proteins from a single transcription unit have become an increasingly common alternative approach. In this case, multi-gene expression is now best implemented by expression from a single promoter, using IRES or viral 2A-like peptide sequences (Szymczak et al. 2004) to "link" the individual transgenes. This solution is limited to a few genes and does not allow independent gene regulation through the use of individual promoters. The invention described here can express multiple genes, each with their own promoter for independent gene regulation. Alternatively, cassettes formed from the coding regions of several genes can be expressed from single transcription units using IRES or viral 2A-like peptide sequences and inserted into the artificial chromosome. These cassettes can then be combined with other cassettes or individual recombinant genes to express substantially greater numbers of recombinant genes from a single artificial chromosome construct.

Another aspect of this invention is the use of a deletion in the artificial chromosome to significantly increase the expression from recombinant genes inserted into the artificial chromosome. Previous practice for expressing a recombinant gene placed within the artificial chromosome has been to insert the coding region into the coding region of a gene within the large genomic DNA cloned within the artificial chromosome or to place the recombinant gene near the promoter of this gene contained within the artificial chromosome. By choosing a genomic region containing an active gene, it was assumed that an "open" chromatin region would be created near the promoter of the gene contained within the artificial chromosome that would be permissive for transcription. Inherent in this assumption is that the primary determinant of the activity of the recombinant gene would be creation of this "open" environment.

We instead find that a distinct structural domain involving the folding of 10 and 30 nm chromatin fibers is created over large domains in the artificial chromosome or even the entire artificial chromosome; however, the nature of this structural domain may represent only a necessary but not sufficient criteria for establishing the expression level or recombinant genes placed within this domain. Other mechanisms may operate as well such that deletions of specific DNA regions within the artificial chromosome would increase expression from recombinant genes placed within the artificial chromosome. We describe a process by which deletions can be made and the expression of a recombinant gene can be measured as a means of identifying deletions that either have no effect or increase expression of the recombinant gene. Deletions of the artificial chromosome can be used to identify the minimal DNA sequences for a given genomic region cloned within the artificial chromosome that are needed to create the permissive environment for expression of the recombinant gene. A smaller artificial chromosome has the advantage of being easier to isolate without damage and also often provides a higher transfection efficiency. Also specific deletions can be identified that lead to significant increases in the expression of recombinant genes placed within the artificial chromosome. We illustrate the latter by describing a 12 fold improved expression per copy of the recombinant gene/artificial chromosome construct by deleting the promoter of a gene contained within the genomic DNA cloned within the artificial chromosome, even though the deleted promoter was a large genomic distance away from the location of the recombinant gene. This increase in expression was unexpected and the mechanism is not yet clear, although it may be related to the phenomenon of transcriptional interference by which transcription of a first gene through a second gene can decrease the expression of the second gene through an effect on the promoter of the second gene, although examples of this in mammalian cells are relatively scarce (Mazo et al. 2007).

However, the actual explanation could be more complicated as RNA FISH using the entire BAC as a probe revealed no significant decrease in total RNA nascent transcripts after promoter deletion.

Below we describe exemplary applications of our invention. Aspects of this invention were disclosed in Bian and Belmont (2010), below, and in abstract and/or oral form, during and/or after the American Society for Cell Biology (ASCB) 49th Annual Meeting, Dec. 5-9, 2009, San Diego, Calif.

EXAMPLES OF THE INVENTION

Example 1

Copy Number Dependent, Position Independent Expression of a mRFP Reporter Gene Inserted at Two Different Locations into a BAC Containing the DHFR Gene Locus We inserted a mRFP reporter gene at two different locations within a 170 kb BAC containing the DHFR locus (Bian and Belmont 2010) (FIG. 1). The DHFR BAC used contains the DHFR gene locus and part of the Msh3 gene locus. Both are transcribed from a divergent promoter located between the two genes. We used a Tn5 transposon system to randomly insert the mRFP reporter gene together with a zeocin selectable marker. Two insertions, C4 and C27, were selected for further study. The C27 and C4 insertions were mapped to nucleotides 23,426 and 117,695 of the Msh3 gene, respectively. Both locations of the mRFP reporter gene were in introns of the Msh3 gene. In clone C27 the mRFP reporter gene is transcribed in the same direction as the Msh3 gene while in clone C4 the mRFP is transcribed in the opposite direction.

After BAC transfection into mouse NIH 3T3 cells, 100% of stable colonies showed significant fluorescence. Mean fluorescence in stably selected cells generated from transfecting the BAC reporter was 1-2 orders of magnitude higher than in stably selected cells from control experiments in which the same reporter cassette, with or without flanking chicken HS4 boundary elements, was transfected as an isolated DNA fragment. A linear relationship between BAC copy number and mRFP fluorescence with a 0.93 correlation coefficient was observed over a range of 1-400 BAC copies (FIG. 2) versus a correlation coefficient of 0.15 for multi-copy insertions of the reporter cassette alone (Bian and Belmont 2010).

Importantly, the expression per BAC/reporter gene copy was essentially independent of chromosome insertion site. Moreover, the expression per copy was essentially the same at two very different locations of the reporter gene within the BAC, covering a wide range of distances from the promoter (23-117 kb).

Using a lac operator/lac repressor tagging system, we visualized the large-scale chromatin organization of the multi-copy BAC insertions in the mouse 3T3 cells (FIG. 3). A 256mer lac operator repeat with a selectable marker was inserted into the DHFR BAC also using a Tn5 transposon. Expression of GFP-lac repressor was used to localize the lac operator repeats within the integrated BAC constructs. The spacing of GFP spots was similar for different insertions of the BAC, independent of chromosome location. In particular, the C4-10 clone with multiple copies of the BAC inserted into centromeric heterochromatin showed similar structure to other cell clones, as indicated by the average spacing of GFP spots (FIG. 3B). Moreover, the expression of the mRFP reporter gene per copy was essentially the same as observed in other clones. Typically, recombinant genes inserted into centromeric heterochromatin are subject to severe gene silencing effects. Centromeric heterochromatin in interphase nuclei is usually condensed, forming "chromocenters" which stain heavily with DNA stains such as DAPI. Therefore the DHFR BAC insertions into centromeric heterochromatin appear to resist both the chromatin condensation and gene silencing associated with centromeric heterochromatin.

Together these results indicate the creation of a distinct structural domain by large regions of the DHFR BAC independent of the chromosome integration site. Moreover, our results also indicate creation of a transcriptionally permissive environment over most of the DHFR BAC, indicating the feasibility of obtaining copy number dependent, chromosome position independent expression for multiple recombinant genes inserted at multiple locations into the DHFR BAC without transcriptional interference between these recombinant genes.

Example 2

Improved Expression of mRFP Reporter Mini-Gene Contained within DHFR BAC by Targeted Deletion of DHFR/Msh3 Divergent Promoter The DHFR BAC contains two transcription units, DHFR and Msh3, both driven by a small (<1 kb) divergent promoter. Homologous recombination was used to make a 2 kb deletion centered around the major DHFR promoter, and deleting both the major and minor DHFR promoters. The original intent of this experiment was to test whether expression from this promoter was required for maintaining a transcriptionally permissive environment and a decondensed, large-scale chromatin organization to the multi-copy BAC insertion. However, instead of observing a decrease in transcription of the mRFP reporter mini-gene, a 12 fold increased expression level of a mRFP reporter transgene placed within a Msh3 intron (C27 insertion, FIG. 1b) was observed with preservation of its copy number dependent, position independent expression (FIG. 4). This was observed for multiple, independent mouse NIH 3T3 stable cell clones, each with the BAC integrated at a different chromosome location. Plotting the mRFP expression level, as measured by flow cytometry measurement of mRFP fluorescence, versus BAC copy number, measured by qPCR, revealed a 12 fold higher slope indicative of a 12 fold higher expression level per copy number of the mRFP mini-gene, independent of chromosome insertion site. This represents a significant improvement in expression level and the capability of the DHFR BAC to be used to obtain high-level expression of recombinant genes inserted within the BAC.

Example 3

Copy Number Dependent, Position Independent Co-expression of Two Mini-genes

As described in example 1, similar reporter gene expression per copy was observed for NIH 3T3 cell clones carrying BACs with a reporter mini-gene inserted at two different locations within the DHFR BAC separated by nearly 100 kbp. This indicates that the DHFR BAC DNA creates a global large-scale chromatin conformation permissive for reporter gene expression. It also indicates that the same approach of inserting a recombinant gene within the BAC could be extended to reproducible, copy number dependent, position independent expression of multiple recombinant genes, without interference in transcription between the recombinant genes as has been observed with traditional plasmid or viral constructs (Curtin et al. 2008). To further confirm this, homologous recombination in *E. Coli* was used to insert two different reporter gene cassettes into the parent DHFR BAC (Bian and Belmont 2010). A CMV promoter-driven EGFP reporter gene cassette containing the kanamycin/neomycin selectable marker was inserted into Msh3 intron 8, the same intron into which the original reporter gene transposon inserted in BAC clone C27 (Example 1). A CMV promoter-driven mRFP reporter gene/zeocin selectable marker cassette was inserted into Msh3 intron 19, the same intron into which the original reporter gene transposon inserted in BAC clone C4 (Example 1). NIH 3T3 cells were transfected with the linearized two-reporter BAC and selected for stable transformants with zeocin. As a control, cells were also transfected with a DNA fragment from a plasmid construct containing the same two mRFP and EGFP expression cassettes.

After selection for stable transformants, cells were analyzed for mRFP and GFP fluorescence using flow cytometry. Stable selection produced a pool of cells derived from many independent cell clones, each with the transfected DNA integrated at different chromosome sites. This pool of cells was analyzed together. Most stable cells with the integrated linear DNA fragment from the plasmid did not express mRFP or GFP above background fluorescence levels of control cells which had not been transfected. Most of the minority of cells showing above background fluorescence levels showed uncorrelated levels of mRFP versus GFP fluorescence, with only a small fraction of these cells showing a linear relationship between mRFP versus GFP fluorescence (FIG. 5). In contrast, nearly all cells derived from the BAC transfection showed above background fluorescence with average fluorescence levels roughly 2 orders of magnitude larger than observed in cells from the plasmid linear fragment transfection. Moreover, in this mixed population of different stable NIH 3T3 cell clones, a near constant ratio of mRFP versus GFP fluorescence was observed (correlation coefficient=0.826), implying that the ratio of expression from these two mini-genes was independent of the chromosome integration site. Flow cytometry of four stable subclones from this mixed population revealed similar ratios of mRFP and GFP expression as seen for the mixed population of cells. Together with the results from example 1 showing copy number dependent expression of a single recombinant gene, these results indicated copy number dependent, position independent expression from two co-expressed mini-genes contained within the DHFR BAC.

The above results showed simultaneous expression of two mini-genes separated by ~100 kb. This raised the question of whether the position within the DHFR BAC of the two mini-genes had a significant impact on their transcriptional activity. To address this question, different modified DHFR BACs were created which kept fixed the location of the GFP reporter mini-gene cassette, but which varied the position of the mRFP reporter cassette. A Tn5 transposon was used to randomly insert the mRFP expression cassette into the DHFR BAC, and six clones were picked and their insertion sites mapped. Each of these BACs were purified and used to transfect mouse NIH 3T3 cells and mixed populations of stable cell clones were obtained from each of these 6 transfections. Flow cytometry (FIG. 6) revealed each of these BACs produced stable cell populations with similar ratios of GFP and mRFP expression, with this ratio varying no more than 2.4 fold over the entire group of 6 BACs.

These results show not only simultaneous expression of two mini-genes at near constant ratios of expression independent of chromosome integration site, but also show that the DHFR BAC supports similar levels of expression from a mini-gene over a large region of the DHFR BAC, indicating a large domain permissive for transcription which spreads throughout the BAC, independent of the mouse chromosome integration site. Our results indicate that additional recombinant genes, beyond two, can be placed at multiple locations throughout the DHFR BAC for simultaneous expression.

Example 4

Expression of Multiple Recombinant Genes from the DHFR BAC and Testing for Improved Induced Pluripotent Stem Cell (iPSC) Creation A critical need for multi-transgene expression is best illustrated by experiences with the highest profile, recent application of multi-gene transgenesis in mammalian cells: generation of induced pluripotent stem cells (iPSCs) through expression of 4 or more factors. A major issue in future applications of this technology remains the low efficiency of reprogramming combined with concerns over genetic modifications associated with reprogramming. Initial demonstration of iPS cell reprogramming used a mixture of lentiviruses, each expressing one of four factors (Okita et al. 2007; Takahashi et al. 2007; Wernig et al. 2007; Yu et al. 2007). Reprogramming efficiency was significantly improved with development of protein cassettes expressing all four factors from a single promoter (Carey et al. 2009; Kaji et al. 2009; Yusa et al. 2009) by connecting sequences of each factor by viral 2A-like peptide sequences which induce ribosome skipping (Szymczak et al. 2004). However, overall reprogramming remained low, suggesting that a stochastic event, in addition to satisfactory expression levels of the four factors, is required for reprogramming. One way to test the correlation between factor expression levels and reprogramming efficiency is through analysis of "secondary" reprogramming of differentiated cells generated from a single iPS cell clone (Hockemeyer et al. 2008; Maherali et al. 2008; Woltjen et al. 2009) or from transgenic mice created from iPS cells (Wernig et al. 2008), or, more recently, from a transgenic mouse carrying an inducible four factor cassette inserted at a specific locus (Carey et al. 2010). Variations in reprogramming efficiency from 1-29% and clear effects of gene dosage and chromosome position effects, including variegated expression, suggest that transgene expression remains a large contributing factor to reprogramming efficiency.

Generation of iPSCs is a natural potential application for the invention of expressing multiple recombinant genes in a copy number dependent, position independent manner by inserting them within a suitable artificial chromosome. To test whether all four factors (myc, Klf4, Sox2, Oct4) can be expressed simultaneously from the DHFR BAC, BAC recombineering was used to insert a selectable marker plus these four recombinant genes, each driven by the same retroviral promoter as used in previous studies, into different locations of the DHFR BAC. RT-PCR demonstrated expression of all four factor mRNAs after transfection into NIH 3T3 cells. Roughly 25% of stable colonies showed an unusual morphology consisting of small, round cells tightly packed into circumscribed patches, a hallmark of the first, mesenchymal to epithelial transition stage of fibroblast iPSC reprogramming (Li et al. 2010).

These results demonstrate the potential of expressing four factors simultaneously from the DHFR BAC. The potential of this modified BAC to induce iPSC reprogramming is confirmed by transfecting this BAC into somatic cells capable of reprogramming and testing the efficiency of reprogramming using established methods. Transfection efficiency of the BAC DNA into primary cells is improved by reducing the overall size of the BAC. As described in Example 2, deletions of the DHFR BAC using homologous recombination in *E. Coli* are made followed by assays of recombinant gene expression. The protocol path is making a deletion, assaying expression of the four factors, and, if the expression of these four factors remains the same or increases, repeating the process until a minimum size is reached that sustains expression of the recombinant genes. A first candidate for a deletion is the promoter deletion described in Example 2, which can increase by an order of magnitude the expression of all four factors. Larger deletions removing bigger segments can also be made.

Larger numbers of recombinant genes can also be expressed using the same DHFR BAC. Therefore additional factors can be added with subsequent tests for improvement in the reprogramming efficiency. Preferred factors include addition of Lin-28, which improves efficiency ~2 fold (Yusa et al. 2009), and expression of UTF1 combined with shRNAi for p53 knockdown, which together can increase iPS cell generation 100 fold (Zhao et al. 2008).

Example 5

Identify BACs and BAC/Promoter Combinations that Support High-level, Stable Transgene Expression Independent of Cell Proliferation or Differentiation Status Transgene silencing is not only a major problem with long-term passaging in culture, but also after transition from a proliferative to quiescent state or after differentiation from one cell lineage or cell type to another. In this example we disclose that resistance to gene silencing with changes in the proliferative state or after differentiation requires a large-scale chromatin domain environment that remains open during these processes, and we further disclose how to identify genomic loci cloned within BACs that are capable of reconstituting an open large-scale chromatin environment in multiple cell types independent of their proliferative status. We provide a detailed experimental path to identify BAC/promoter combinations that produce copy number dependent, position independent expression of multiple transgenes placed at appropriate locations within these BACs independent of the cell differentiation or proliferative state.

The first step is to survey different constitutive promoters for use in the original DHFR BAC clone, as used in Examples 1-3. We also include commonly used promoters such as CMV and SV40 as well as endogenous promoters from human genes, including the commonly used β-actin, ubiquitin, E1A, and GAPDH promoters. We also include a set of 4-12 promoters identified as showing the most constant expression levels across a wide range of rat tissue types based on a combined DNA chip and RT-qPCR survey (Cai et al. 2007), as well as the U83175 (Rosa26) and Setd5 promoters from the Rosa26 locus.

Using these promoters to drive fluorescent protein reporter genes, we use single and dual reporter gene assays (as described in Example 3, FIGS. 5 & 6) to monitor expression of these reporter genes. For each promoter we examine multiple BAC insertion sites of the GFP reporter gene to determine the degree to which the promoter activity is independent of position within the DHFR BAC. AC constructs are tested initially in mouse NIH 3T3 cells that have a high transfection and cloning efficiency; although immortal, these cells retain aspects of normal growth regulation, including contact inhibition and anchorage dependence.

We identify a set of promoters of variable strengths capable of conferring copy number dependent, position independent expression within the context of the DHFR BAC. We also make a direct comparison between the transcriptional activity of each of these promoters when removed from their normal chromosomal context and placed in the DHFR gene locus environment, confirming that copy number dependent, position independent expression is a general property for promoters placed within the DHFR gene locus. We identify which promoters are most resistant to epigenetic gene silencing over repeated cell passsaging in vitro.

The second step is to test the subset of promoters that are most promising in BACs containing different genomic regions. For instance, reporter activity is tested after insertion into genomic regions cloned within BACs from active gene loci such as that flanking the DHFR, ubiquitin, E3A, GPDH3 gene loci, as well as loci encompassing genes expressed ubiquitously in most tissues including the Rosa26, Ppib, March5, B2m, Hmbs, and Mapk14 loci. These measurements are made for proliferating cultures and for quiescent cells arrested in G0 by serum starvation or contact inhibition.

The third step, starting with the subset of the most promising BAC/promoter combinations tested in steps 1 & 2, is to create mouse ES cell lines stably transfected with these BACs. Using several differentiation protocols, including into fibroblast-like cells (Sinclair et al. 2010), erythroblasts (Nakano et al. 1996), and neuronal precursors (Kim et al. 2009), we screen for invariance of reporter gene expression during differentiation into different cell lineages. For preferred candidates this is followed by a more thorough examination of different cell types using formation of embryoid bodies, and then, mouse teratomas. A final screen is in transgenic mice, assaying expression levels of reporter genes in different tissues.

This protocol establishes the overall dynamic range of position effects experienced by specific promoters when placed in different chromatin environments established by different BACs. We also identify BAC/promoter combinations which support long-term, stable, copy number dependent, position independent expression from multiple transgenes independent of proliferative or differentiated state.

These in vitro experiments in mouse cells can then be replicated using human cell lines and human ES cells as well, while results from transgenic mice provide an additional initial test of BAC/promoter combinations that could be used in humans.

The end result of these protocols is the identification of promoters of varying strengths and BAC clones useful for simultaneous expression of multiple recombinant genes that are largely invariant during changes in cell proliferation or differentiation. The same protocol may used for alternative species.

Example 6

Cell Type or Cell Cycle Specific or Inducible Expression of Multiple Recombinant Genes In the preceding examples we have described constitutive expression of multiple recombinant genes by inserting them into the appropriate BAC that is chosen to maintain an open, large-scale chromatin environment conducive to transcription. However, there are many cases in which one would like to express multiple recombinant genes in specific cell types (not necessarily the same) and/or at specific cell cycle stages. Embodiments of this invention can also carry out this goal.

In one aspect we replace the constitutive promoters driving the recombinant genes placed within the BAC used in the preceding examples with promoters that are active in a particular cell type or cell cycle stage or promoters that can be induced by specific chemicals or environmental conditions (i.e. heat shock or heavy metal exposure). There are extensive precedents confirming the feasibility of this approach, such as where specifically several kbp of upstream sequence from a given gene was incorporated with the proximal promoter (the several hundred by immediately upstream of a gene) to drive the expression of a recombinant gene in a similar pattern to the endogenous gene. For example, a 4 kb human Oct4 promoter fragment drives EGFP expression in hESCs, serving as an in vivo pluripotency marker paralleling endogenous Oct 4 expression (Gerrard et al. 2005). Typically, these several kbp promoters can drive expression with similar but not identical patterns as the endogenous gene. The differences are attributed to chromosomal position effects. Consistent with our earlier examples, embedding recombinant genes within a suitable BAC which creates an open, large-scale chromatin environment when integrated into the host genome provides a reproducible environment for expression of recombinant genes independent of the chromosome integration site. Using candidate promoter regions from endogenous genes which show the desired expression pattern, we can use the fluorescent reporter gene approach and test these promoter regions for their capability of driving the appropriate expression patterns of recombinant genes when embedded within a suitable BAC, using experimental approaches as described in preceding examples. With such appropriate promoter/BAC combinations identified using fluorescent reporter genes, we can apply the same promoter/BAC combinations to express the desired recombinant genes. Preferred BACs are similar to those tested in Example 5 which contain genomic regions from active gene loci such as that flanking the DHFR, ubiquitin, E3A, GPDH3 gene loci, as well as loci encompassing genes expressed ubiquitously in most tissues including the Rosa26, Ppib, March5, B2m, Hmbs, and Mapk14 loci.

This first approach greatly reduces the variegation and position effects seen with traditional approaches for recombinant gene expression, allowing expression of multiple recombinant genes. In particular by choosing different promoter regions for different genes, we can construct BAC/recombinant gene combinations in which the same construct expresses a subset of recombinant genes in a particular tissue or cell type or at a specific cell cycle stage which is different from the expression patterns of other recombinant genes expressed on the same construct. For instance, in a straightforward application of this technology, we can make a multiple reporter gene construct that reflects the cell proliferation status and/or differentiation state. A major theme today in regenerative biology is identifying small molecules in high throughput drug screens to steer differentiation of cells along a particular pathway. The efficiency of such screens is be greatly enhanced through use of a cell line expressing multiple cell lineage fluorescent markers. Another application of this technology is to build synthetic gene networks, where multiple components of this network need to be expressed at predictable relative levels.

In the case where single or multiple recombinant genes are to be expressed in the same differentiated and/or proliferative stage, the invention provides yet another solution. As in the first approach, constitutive promoters are replaced with promoters that are active in a particular cell type or cell cycle stage. However, in this second approach, rather than choose a BAC containing a genomic region predicted as forming an open, large-scale chromatin environment permissive for expression of recombinant genes in most cell types instead a BAC is chosen containing a genomic region predicted as forming an open, large-scale chromatin environment in a particular cell type and/or cell cycle stage. BACs containing genomic regions surrounding gene loci known to be active in the chosen cell type and or cell cycle stage are selected for screening using a fluorescent reporter gene approach as outlined previously for the first approach. Here the solution is to select BACs which maximize expression from a constitutive promoter in the desired cell type or cell cycle stage while minimizing expression in other differentiated or proliferative states. Such BACs are then combined with suitable promoters active in the selected/targeted cell type or cell cycle stage.

This second approach provides improved overall gene regulation of the recombinant genes including repression of expression in untargeted/inappropriate cell type or proliferative stage.

REFERENCES

Antoch M P, Song E J, Chang A M, Vitaterna M H, Zhao Y, Wilsbacher L D, Sangoram A M, King D P, Pinto L H, Takahashi J S (1997) Functional identification of the mouse circadian Clock gene by transgenic BAC rescue. Cell 89: 655-667

Antoniou M, Harland L, Mustoe T, Williams S, Holdstock J, Yague E, Mulcahy T, Griffiths M, Edwards S, Ioannou P A, Mountain A, Crombie R (2003) Transgenes encompassing dual-promoter CpG islands from the human TBP and HNRPA2B1 loci are resistant to heterochromatin-mediated silencing. Genomics 82: 269-279

Barron N, Piskareva O, Muniyappa M (2007) Targeted genetic modification of cell lines for recombinant protein production. Cytotechnology 53: 65-73

Bharadwaj R R, Trainor C D, Pasceri P, Ellis J (2003) LCR-regulated transgene expression levels depend on the Oct-1 site in the AT-rich region of beta-globin intron-2. Blood 101: 1603-1610

Bian Q, Belmont A S (2010) BAC TG-EMBED: one-step method for high-level, copy-number-dependent, position-independent transgene expression. Nucleic Acids Res 38: e127

Blaas L, Musteanu M, Eferl R, Bauer A, Casanova E (2009) Bacterial artificial chromosomes improve recombinant protein production in mammalian cells. BMC Biotechnol 9: 3

Boyle A P, Davis S, Shulha H P, Meltzer P, Margulies E H, Weng Z, Furey T S, Crawford G E (2007) High-resolution mapping and chraracterization of open chromatin across the genome. Cell 132: 311-322

Boyle A P, Furey T S (2009) High-resolution mapping studies of chromatin and gene regulatory elements. Epigenomics 1: 319-329

Cacciatore J J, Chasin L A, Leonard E F (2010) Gene amplification and vector engineering to achieve rapid and high-level therapeutic protein production using the Dhfr-based CHO cell selection system. Biotechnol Adv Cai J H, Deng S, Kumpf S W, Lee P A, Zagouras P, Ryan A, Gallagher D S (2007) Validation of rat reference genes for improved quantitative gene expression analysis using low density arrays. Biotechniques 42: 503-12

Carey B W, Markoulaki S, Beard C, Hanna J, Jaenisch R (2010) Single-gene transgenic mouse strains for reprogramming adult somatic cells. Nat Methods 7: 56-9

Carey B W, Markoulaki S, Hanna J, Saha K, Gao Q, Mitalipova M, Jaenisch R (2009) Reprogramming of murine and human somatic cells using a single polycistronic vector. Proc Natl Acad Sci USA 106: 157-62

Chung J H, Whiteley M, Felsenfeld G (1993) A 5' element of the chicken beta-globin domain serves as an insulator in human erythroid cells and protects against position effect in Drosophila. Cell 74: 505-514

Curtin J A, Dane A P, Swanson A, Alexander I E, Ginn S L (2008) Bidirectional promoter interference between two widely used internal heterologous promoters in a late-generation lentiviral construct. Gene Ther 15: 384-90

Gerrard L, Zhao D, Clark A J, Cui W (2005) Stably transfected human embryonic stem cell clones express OCT4-specific green fluorescent protein and maintain self-renewal and pluripotency. Stem Cells 23: 124-33

Giel-Moloney M, Krause D S, Chen G, Van Etten R A, Leiter A B (2007) Ubiquitous and uniform in vivo fluorescence in ROSA26-EGFP BAC transgenic mice. Genesis 45: 83-9

Grosveld F, van Assendelft G B, Greaves D R, Kollias G (1987) Position-independent, high-level expression of the human beta-globin gene in transgenic mice. Cell 51: 975-985

Guy L G, Kothary R, DeRepentigny Y, Delvoye N, Ellis J, Wall L (1996) The beta-globin locus control region enhances transcription of but does not confer position-independent expression onto the lacZ gene in transgenic mice. Embo J 15: 3713-21

Heintz N (2000) Analysis of mammalian central nervous system gene expression and function using bacterial artificial chromosome-mediated transgenesis. Human molecular genetics 9: 937-943

Hockemeyer D, Soldner F, Cook E G, Gao Q, Mitalipova M, Jaenisch R (2008) A drug-inducible system for direct reprogramming of human somatic cells to pluripotency. Cell Stem Cell 3: 346-53

Kaji K, Norrby K, Paca A, Mileikovsky M, Mohseni P, Woltjen K (2009) Virus-free induction of pluripotency and subsequent excision of reprogramming factors. Nature 458: 771-5

Kim J M, Kim J S, Park D H, Kang H S, Yoon J, Baek K, Yoon Y (2004) Improved recombinant gene expression in CHO cells using matrix attachment regions. Journal of Biotechnology 107: 95-105

Kim M, Habiba A, Doherty J M, Mills J C, Mercer R W, Huettner J E (2009) Regulation of mouse embryonic stem cell neural differentiation by retinoic acid. Dev Biol 328: 456-71

Kwaks T H, Barnett P, Hemrika W, Siersma T, Sewalt R G, Satijn D P, Brons J F, van Blokland R, Kwakman P, Kruckeberg A L, Kelder A, Otte A P (2003) Identification of anti-repressor elements that confer high and stable protein production in mammalian cells. Nature biotechnology 21: 553-558

Kwaks T H J, Otte A P (2006) Employing epigenetics to augment the expression of therapeutic proteins in mammalian cells. Trends Biotechnology 24: 137-142

Li R, Liang J, Ni S, Zhou T, Qing X, Li H, He W, Chen J, Li F, Zhuang Q, Qin B, Xu J, Li W, Yang J, Gan Y, Qin D, Feng S, Song H, Yang D, Zhang B, Zeng L, Lai L, Esteban M A, Pei D (2010) A mesenchymal-to-epithelial transition initiates and is required for the nuclear reprogramming of mouse fibroblasts. Cell Stem Cell 7: 51-63

Lusky M, Botchan M (1981) Inhibition of SV40 replication in simian cells by specific pBR322 DNA sequences. Nature 293: 79-81

Maherali N, Ahfeldt T, Rigamonti A, Utikal J, Cowan C, Hochedlinger K (2008) A high-efficiency system for the generation and study of human induced pluripotent stem cells. Cell Stem Cell 3: 340-5

Mao X, Fujiwara Y, Chapdelaine A, Yang H, Orkin S H (2001) Activation of EGFP expression by Cre-mediated excision in a new ROSA26 reporter mouse strain. Blood 97: 324-326

Mazo A, Hodgson J W, Petruk S, Sedkov Y, Brock H W (2007) Transcriptional interference: an unexpected layer of complexity in gene regulation. J Cell Sci 120: 2755-61

Nakano T, Kodama H, Honjo T (1996) In vitro development of primitive and definitive erythrocytes from different precursors. Science 272: 722-4

Okita K, Ichisaka T, Yamanaka S (2007) Generation of germline-competent induced pluripotent stem cells. Nature 448: 313-7

Peterson D O, Beifuss K K, Morley K L (1987) Context-dependent gene expression: cis-acting negative effects of specific procaryotic plasmid sequences on eucaryotic genes. Mol Cell Biol 7: 1563-7

Pikaart M J, Recillas-Targa F, Felsenfeld G (1998) Loss of transcriptional activity of a transgene is accompanied by DNA methylation and histone deacetylation and is prevented by insulators. Genes Dev 12: 2852-62

Rubin J E, Pasceri P, Wu X, Leboulch P, Ellis J (2000) Locus control region activity by 5'HS3 requires a functional interaction with beta-globin gene regulatory elements: expression of novel beta/gamma-globin hybrid transgenes. Blood 95: 3242-3249

Sinclair P, Bian Q, Plutz M, Heard E, Belmont A S (2010) Dynamic plasticity of large-scale chromatin structure revealed by self-assembly of engineered chromosome regions. J Cell Biol 190: 761-776

Stamatoyannopoulos J A, Clegg C H, Li Q (1997) Sheltering of gamma-globin expression from position effects requires both an upstream locus control region and a regulatory element 3' to the A gamma-globin gene. Mol Cell Biol 17: 240-7

Szymczak A L, Workman C J, Wang Y, Vignali K M, Dilioglou S, Vanin E F, Vignali D A (2004) Correction of multi-gene deficiency in vivo using a single 'self-cleaving' 2A peptide-based retroviral vector. Nat Biotechnol 22: 589-94

Takahashi K, Tanabe K, Ohnuki M, Narita M, Ichisaka T, Tomoda K, Yamanaka S (2007) Induction of pluripotent stem cells from adult human fibroblasts by defined factors. Cell 131: 861-872

Truffinet V, Guglielmi L, Cogne M, Denizot Y (2005) The chicken beta-globin HS4 insulator is not a silver bullet to obtain copy-number dependent expression of transgenes in stable B cell transfectants. Immunology letters 96: 303-304

Utikal J, Polo J M, Stadtfeld M, Maherali N, Kulalert W, Walsh R M, Khalil A, Rheinwald J G, Hochedlinger K (2009) Immortalization eliminates a roadblock during cellular reprogramming into iPS cells. Nature 460: 1145-8 van Gaal E V B, Hennink W E, Crommelin D J A, Mastrobattista E (2006) Plasmid engineering for controlled and sustained gene expression fo nonviral gene therapy. Pharm Res 23: 1053-1074

Walsh G (2004) Biopharmeceuticals: approvals and approval trends in 2004. BioPharm International Wernig M, Lengner C J, Hanna J, Lodato M A, Steine E, Foreman R, Staerk J, Markoulaki S, Jaenisch R (2008) A drug-inducible transgenic system for direct reprogramming of multiple somatic cell types. Nat Biotechnol 26: 916-24

Wernig M, Meissner A, Foreman R, Brambrink T, Ku M, Hochedlinger K, Bernstein B E, Jaenisch R (2007) In vitro reprogramming of fibroblasts into a pluripotent ES-cell-like state. Nature 448: 318-24

Williams S, Mustoe T, Mulcahy T, Griffiths M, Simpson D, Antoniou M, Irvine A, Mountain A, Crombie R (2005) CpG-island fragments from the HNRPA2B1/CBX3 genomic locus reduce silencing and enhance transgene expression from the hCMV promoter/enhancer in mammalian cells. BMC biotechnology 5: 17

Woltjen K, Michael I P, Mohseni P, Desai R, Mileikovsky M, Hamalainen R, Cowling R, Wang W, Liu P, Gertsenstein M, Kaji K, Sung H K, Nagy A (2009) piggyBac transposition reprograms fibroblasts to induced pluripotent stem cells. Nature 458: 766-70

Yang X W, Model P, Heintz N (1997) Homologous recombination based modification in *Escherichia coli* and germline transmission in transgenic mice of a bacterial artificial chromosome. Nat Biotechnol 15: 859-65

Yu J, Vodyanik M, Smuga-Otto K, Antogiewicz-Bourget J, Frane J L, Tian S, Nie J, Jonsdottir G A, Ruotti V, Stewart R, Slukvin I L, Thompson J A (2007) Induced pluripotent stem cell lines derived from human somatic cells. Science 318: 1917-1920

Yusa K, Rad R, Takeda J, Bradley A (2009) Generation of transgene-free induced pluripotent mouse stem cells by the piggyBac transposon. Nat Methods 6: 363-9

Zahn-Zabal M, Kobr M, Girod P A, Imhof M, Chatellard P, de Jesus M, Wurm F, Mermod N (2001) Development of stable cell lines for production or regulated expression using matrix attachment regions. Journal of Biotechnology 87: 29-42

Zhao Y, Yin X, Qin H, Zhu F, Liu H, Yang W, Zhang Q, Xiang C, Hou P, Song Z, Liu Y, Yong J, Zhang P, Cai J, Liu M, Li H, Li Y, Qu X, Cui K, Zhang W, Xiang T, Wu Y, Zhao Y, Liu C, Yu C, Yuan K, Lou J, Ding M, Deng H (2008) Two supporting factors greatly improve the efficiency of human iPSC generation. Cell Stem Cell 3: 475-9

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. An in vitro method for expressing multiple recombinant genes, comprising:
    a) inserting multiple, different transgenes, each into a separate insertion site of a dihydrofolate reductase (DHFR) genomic region cloned within an artificial chromosome, wherein the transgenes are exogenous to the genomic region, wherein the insertion sites are separated by 23-117 kb;
    b) introducing the artificial chromosome into a eukaryotic cell, wherein the genomic region integrates into a host chromosome of the cell; and
    c) culturing the cell wherein each transgene is expressed copy number dependently and position independently with respect to the integrated genomic region, wherein the integrated genomic region is in open chromatin conformation, and wherein the transgenes are expressed as corresponding proteins.

2. The method of claim 1, wherein the different multiple transgenes are expressed from different promoters.

3. The method of claim 1, wherein the different multiple transgenes are expressed from different promoters, and the transgenes maintain a reproducible relative expression with respect to each other, according to the promoters used to drive each transgene.

4. The method of claim 1, wherein the method comprises inserting the transgenes into the artificial chromosome by homologous recombination.

5. The method of claim 1, wherein the method comprises inserting the transgenes into the artificial chromosome using a transposon and thereby achieving random but high efficiency insertion.

6. The method of claim 1, further comprising step of isolating the proteins.

7. The method of claim 1, wherein the proteins are serum proteins selected from the group consisting of immunoglobulins or fragments thereof, albumin, blood factors, polypeptide hormones, cytokines, chemokines, enzymes and growth factors.

8. The method of claim 1, wherein the transgenes are mini-genes.

9. The method of claim 1, further comprising detecting copy number dependent and position independent expression of the transgenes.

* * * * *